(12) United States Patent
Hoffman

(10) Patent No.: US 6,956,925 B1
(45) Date of Patent: Oct. 18, 2005

(54) METHODS AND SYSTEMS FOR MULTI-MODALITY IMAGING

(75) Inventor: David Michael Hoffman, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/812,152

(22) Filed: Mar. 29, 2004

(51) Int. Cl.[7] .............................................. A61B 6/00
(52) U.S. Cl. ............................... 378/4; 378/11; 378/63
(58) Field of Search .............................. 378/4, 19, 62, 378/63, 11; 250/363.03, 363.04, 363.05, 250/363.01, 363.02; 600/407, 427

(56) References Cited

U.S. PATENT DOCUMENTS

| | | | |
|---|---|---|---|
| 3,965,353 A | 6/1976 | Macovski | 378/6 |
| 4,052,620 A | 10/1977 | Brunnett | 378/97 |
| 4,124,804 A | 11/1978 | Mirell | 378/6 |
| 4,150,292 A | 4/1979 | Ter-Pogossian | 250/363.03 |
| 4,628,356 A | 12/1986 | Spillman et al. | 378/98.8 |
| 4,896,342 A | 1/1990 | Harding | 378/87 |
| 4,956,856 A | 9/1990 | Harding | 378/88 |
| 5,940,468 A | 8/1999 | Huang et al. | 378/57 |
| 6,490,476 B1 * | 12/2002 | Townsend et al. | 600/427 |
| 6,556,653 B2 | 4/2003 | Hussein | 378/90 |
| 6,661,865 B1 * | 12/2003 | Popilock | 378/19 |

\* cited by examiner

*Primary Examiner*—Edward J. Glick
*Assistant Examiner*—Courtney Thomas
(74) *Attorney, Agent, or Firm*—Carl B. Horton, Esq.; Armstrong Teasdale LLP

(57) ABSTRACT

A method of examining a patient is provided. The method includes imaging a patient utilizing a computed tomography imaging modality, the patient between the pencil-beam x-ray source and the x-ray detector, and imaging the patient between the pencil-beam x-ray source and the x-ray detector using a nuclear medicine imaging modality.

38 Claims, 2 Drawing Sheets

METHODS AND SYSTEMS FOR MULTI-MODALITY IMAGING

BACKGROUND OF THE INVENTION

This invention relates generally to imaging systems capable of operation in multiple modalities, and more particularly to methods and systems for conducting a pencil-beam computed tomography (CT) scan in a multi-modality system.

Multi-modality imaging systems are capable of scanning using different modalities, such as, for example, positron emission tomography (PET), single positron emission tomography (SPECT), computed tomography (CT), static x-ray imaging, and dynamic (fluoroscopy) x-ray imaging. In a multi-modal system (also referred to as a multi-modality system), a portion of the same hardware is utilized to perform different scans (e.g., an image produced by SPECT is processed and displayed respectively, by the same computer and display, as an image produced by CT). However, the data acquisition systems (also referred to as an "imaging assembly") are different. For example, on a CT/SPECT system, a radiation source and a radiation detector are used in combination to acquire CT data, while a radiopharmaceutical is typically employed in combination with a SPECT camera to acquire SPECT data.

CT imaging is typically performed using a relatively expensive x-ray source and x-ray detector. A relatively less expensive CT imaging system is a pencil-beam CT system wherein a relatively narrow, cylindrical beam of x-rays are directed towards a relatively inexpensive detector. A pencil-beam CT system architecture facilitates reducing x-ray scatter, producing a relatively high quality image. However, a scan using a pencil-beam CT system typically takes a longer amount of time than scans using typical CT systems. Specifically, emission scans, for example, PET and SPECT scans, typically take several minutes, for example, approximately twenty minutes, whereas a transmission scan, for example, a CT scan, typically takes only several seconds, for example, approximately fifteen seconds.

BRIEF DESCRIPTION OF THE INVENTION

In one embodiment, a method of examining a patient is provided. The method includes imaging a patient utilizing a computed tomography imaging modality, the patient between the pencil-beam x-ray source and the x-ray detector, and imaging the patient between the pencil-beam x-ray source and the x-ray detector using a nuclear medicine imaging modality.

In another embodiment, a multi-modality computed tomography system is provided. The system includes a gantry, rotatable around a viewing area, a x-ray source coupled to the gantry that provides a pencil-beam of x-rays, the x-ray source configured to direct at least a portion of the pencil-beam of x-rays into the viewing area, a detector that is responsive to the pencil-beam of x-rays and that is configured to receive at least a portion of the x-rays during a x-ray computed tomography portion of a scan, and a gamma camera configured to receive gamma photons emitted in the viewing area.

DETAILED DESCRIPTION OF THE INVENTION

Figure 1:
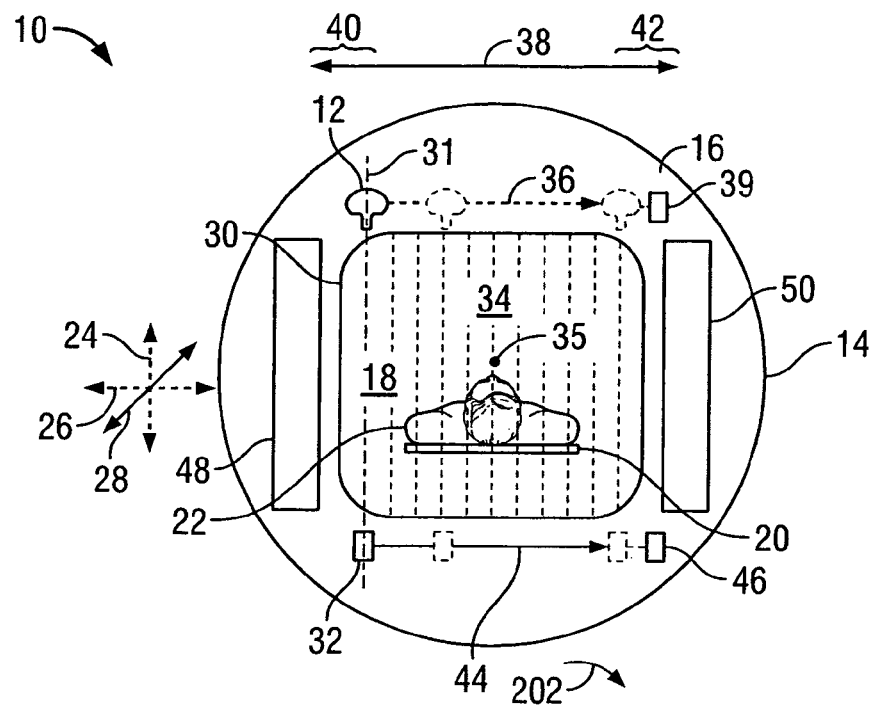
FIG. 1 is a schematic illustration of an imaging system in accordance with an exemplary embodiment of the present invention.

FIG. 1 is a schematic illustration of an imaging system 10 in accordance with an exemplary embodiment of the present invention. Imaging system 10 includes a x-ray source 12 mounted on a gantry 14. In the exemplary embodiment, gantry 14 includes a body 16 having an aperture 18 therethrough. In an alternative embodiment, gantry 14 may be fabricated from a plurality of gantry segments that may be separated from an adjacent segment by a space. A patient table 20 is configured to support and carry a patient 22 in a plurality of viewing positions within aperture 18. Patient table 20 includes a support mechanism (not shown) that is configured to support patient table 20 and move patient table 20 in any of at least three substantial orthogonal directions, including, for example, an up-down direction 24, a right-left direction 26 and a in-out direction 28. The support mechanism may control the motion of patient table 20 prior to a scan to align patient 22, during a scan to control a portion of patient 22 being imaged, and generally during any portion of a scan.

In operation, x-ray source 12 is configured to generate and transmit a pencil-beam of x-rays 30 from a first side of gantry 14 to a second opposite side of gantry 14 along, a detector-source axis 31, to an x-ray detector 32. An area between x-ray source 12 and x-ray detector 32 is a viewing area 34. A longitudinal axis 35 of viewing area 34 is substantially equidistant between x-ray source 12 and x-ray detector 32. This pencil X-ray beam 30 may be attenuated by patient 22 on patient table 20, and the unattenuated x-rays are absorbed by x-ray detector 32. In the exemplary embodiment, x-ray detector 32 comprises a single detector, and x-ray source 12 is a single x-ray source mounted to gantry 14 through a translation mechanism 36 that controls a motion of x-ray source 12 in a laterally translational direction 38. Translation mechanism 36 is configured to move x-ray source using actuator 39 from a first position 40 to a second position 42 continuously at a selectable speed, or incrementally at selectable increments. Pencil-beam of x-rays 30 may be directed to x-ray detector 32 positioned on gantry 14 through a detector translational mechanism 44 that may be controlled using actuator 46 to move detector 32 in cooperation with x-ray source 30 such that detector 32 maintains a relative position (e.g., generally opposite side of viewing area 34) with respect to x-ray source 30 during a scan. In an alternative embodiment, translation mechanism 36 is configured to direct x-ray source 12 along an arcuate path, such as a circumferential path with respect to a substantially constant radius from longitudinal axis 35 of viewing area 34.

Gantry 14 also includes at least one gamma camera 48 mounted to gantry body 16 such that gammas emitted from a radiopharmaceutical within patient 22 are absorbed in gamma camera 48. In the exemplary embodiment, gantry 14 includes a second gamma camera 50 that is mounted on gantry 14 opposite gamma camera 48 such that gamma cameras 48 and 50 may cooperate to detect coincident emissions of gammas, for example, for use in PET imaging. Longitudinal axis 35 of viewing area 34 is substantially equidistant between gamma cameras 48 and 50. In an alternative embodiment, an output of gamma camera 50 is not used, such as when performing certain SPECT imaging scans.

In an alternative embodiment, gamma cameras 48 and 50 are mounted on a second gantry (not shown) that is axially spaced from gantry body 16 such that gamma cameras 48 and 50 may rotate about longitudinal axis 35 in a plane that is parallel to and adjacent to a plane of rotation of gantry body 16. Accordingly, the second gantry may be controlled to scan patient 22 separately and independently from a scan of patient 22 using gantry body 16. For example, gantry body 16 may rotate at a rate that facilitates performing a pencil-beam CT scan and the second gantry may rotate at a rate different that the rate of gantry body 16 that facilitates performing a gamma camera, PET, and/or SPECT scan.

In operation, gamma cameras 48 and 50 may be used during a pencil-beam CT portion of a scan to perform a concurrent gamma camera scan, PET scan, and/or SPECT scan. Gamma cameras 48 and 50 rotate with gantry 14 such that during a pencil-beam CT scan wherein gantry 14 may translate x-ray source 12 and x-ray detector 32 during a portion of the scan and rotate gantry 14 during another portion of the CT scan, gamma cameras 48 and 50 may also perform a nuclear medicine scan, including but, not limited to SPECT and PET.

A group of x-ray attenuation measurements, for example, projection data, from x-ray detector 32 at one gantry angle is referred to as a view. A scan of patient 22 includes a set of views acquired at different gantry angles during one revolution of pencil-beam x-ray source 12 and x-ray detector 32. Gantry 14 rotates around subject to scan patient 22 from different directions to obtain a variety of views of patient 22. Similarly, a group of emission gamma attenuation measurements, for example, emission data from gamma cameras 48 and/or 50 at one gantry angle is referred to as a view. An emission scan of patient 22 includes a set of views acquired at different gantry angles during one revolution of gamma cameras 48 and/or 50.

Figure 2:
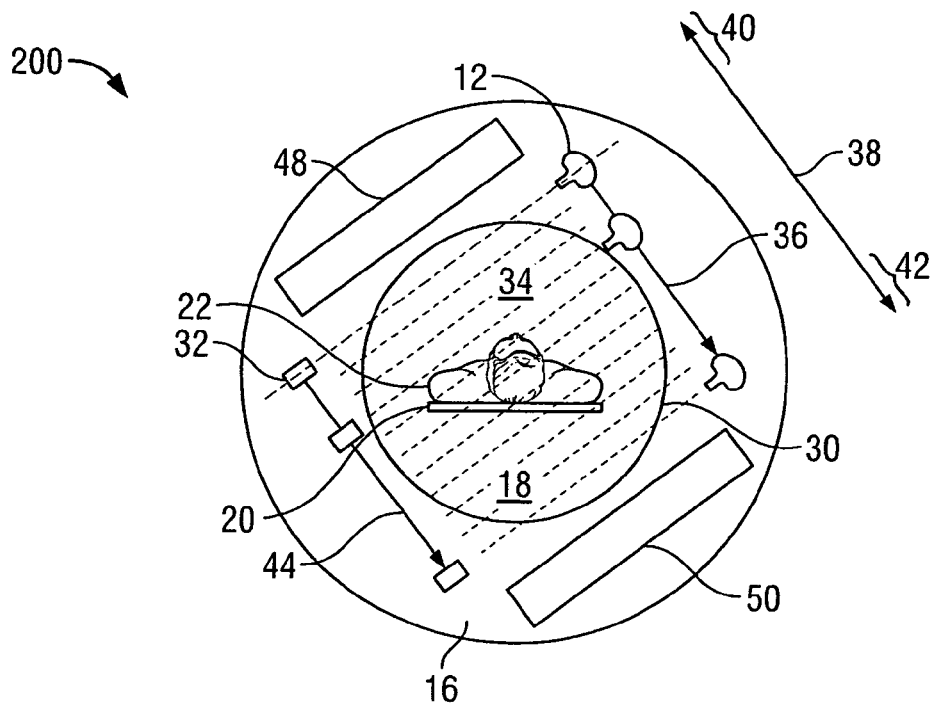
FIG. 2 is a schematic illustration of the imaging system shown in FIG. 1 wherein the gantry has rotated to a second scan position.

FIG. 2 is a schematic illustration of imaging system 10 (shown in FIG. 1) wherein gantry 14 has rotated to a second scan position 200. Imaging system 10 rotated to second scan position 200 is substantially similar to imaging system 10 (shown in FIG. 1) and components of imaging system 10 rotated to a second scan position 200 that are identical to components of imaging system 10, (shown in FIG. 1) are identified in FIG. 2 using the same reference numerals used in FIG. 1.

In the exemplary embodiment, gantry is rotated a selectable number of degrees in a direction of rotation 202. Components mounted on gantry 14, such as, gamma cameras 48 and 50, x-ray source 12 and x-ray detector 32 rotate with gantry 14. In second scan position 200, gamma cameras 48 and 50 and x-ray source 12 and x-ray detector 32 are aligned to provide a second view of patient 22. Patient table 20 may be moved during a scan such that, gamma cameras 48 and 50 and x-ray source 12 and x-ray detector 32 may be provided with other views of patient 22 with gantry 14 held stationary. Gantry 14 may be held in a substantially stationary position while a second portion of a scan is performed.

In operation, gamma cameras 48 and 50 may be used during a pencil-beam CT portion of a scan to perform a concurrent gamma camera scan, PET scan, and/or SPECT scan. Gamma cameras 48 and 50 rotate with gantry 14 such that during a pencil-beam CT scan wherein gantry 14 may translate x-ray source 12 and x-ray detector 32 during a portion of the scan and rotate gantry 14 during another portion of the CT scan, gamma cameras 48 and 50 may also perform a nuclear medicine scan, including but, not limited to SPECT and PET.

Figure 3:
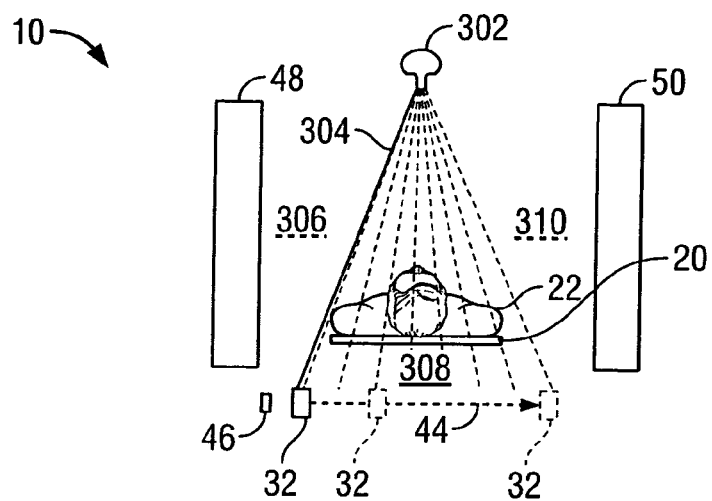
FIG. 3 is a schematic illustration of another embodiment of the imaging system shown in FIG. 1.

FIG. 3 is a schematic illustration of another embodiment of imaging system 10 (shown in FIG. 1). In the exemplary embodiment, imaging system 10 includes a x-ray source 302 configured to sweep a pencil-beam 304 of x-rays from a first side 306 of a viewing area 308 to a second side 310 of viewing area 308. Pencil-beam 304 of x-rays may be directed toward x-ray detector 32, which is positioned laterally using detector translational mechanism 44. Actuator 46 controls detector translational mechanism 44 to move detector 32 in cooperatively with pencil-beam 304 such that detector 32 is maintained in a position to intersect pencil-beam 304 during a CT portion of a scan.

Figure 4:
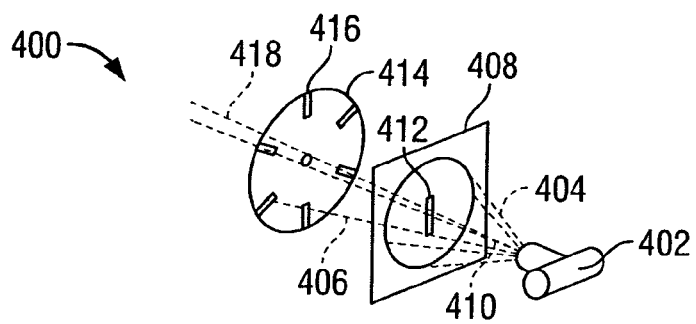
FIG. 4 is a perspective view of an exemplary pencil-beam x-ray source that may be used with the imaging system shown in FIG. 3.

FIG. 4 is a perspective view of an exemplary pencil-beam x-ray source 400 that may be used with imaging system 10 (shown in FIG. 3). A x-ray tube 402 provides a substantially conical beam 404 of x-rays that is collimated into a fan beam 406 by a slit collimator 408 oriented substantially perpendicular to a central axis 410 of conical beam 404. Slit collimator 408 includes a slit 412 positioned such that a portion of x-rays in conical beam 404 pass through slit 412 and are incident upon a rotatable collimating disc 414. Collimating disc 414 includes at least one slit 416 positioned such that during a rotation of collimating disc 414, at least a portion of slit 416 intersects at least a portion of fan beam 406 during a portion of the rotation of collimating disc 414. The size of slits 412 and 416 define a cross-sectional dimension of a pencil-beam 418 of x-rays that may be directed toward a target. An orientation and position of slits 412 and 416 may define a sweep angle wherein the sweep angle is the angular difference between the direction of pencil-beam 418 and central axis 410. A sweep frequency may be determined by, for example, the speed of rotation of collimating disc 414.

Figure 5:
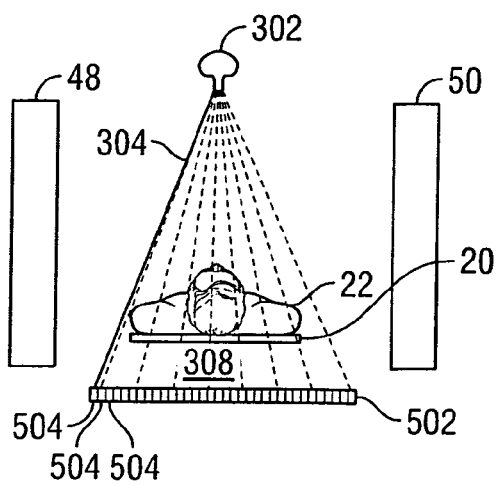
FIG. 5 is a schematic illustration of another embodiment of the imaging system shown in FIG. 3.

FIG. 5 is a schematic illustration of another embodiment of imaging system 10 (shown in FIG. 3). In the exemplary embodiment, components of imaging system 10 shown in FIG. 3 are substantially similar to components of imaging system 10 shown in FIG. 5. Components shown in FIG. 3 that are substantially identical to components shown in FIG. 5 are identified with the same reference numerals in FIG. 5 used in FIG. 3. Imaging system 10 includes a sweeping pencil-beam x-ray source 302 positioned opposite a linear x-ray detector. Source 302 projects pencil-beam 304 of x-rays that is collimated to sweep across viewing area 308. The x-ray beam 304 passes through patient 22 and table 20 to generate an attenuated radiation beam. The attenuated radiation beam impinges upon linear detector array 502. The intensity of the attenuated radiation beam received at a detector array 502 is dependent upon the attenuation of x-ray beam 304 by patient 22 and patient table 20. Each detector element 504 of detector array 502 produces a separate electrical signal that is a measurement of the attenuation by detector array 502. The attenuation measurements from all detector elements 504 are acquired separately to produce a transmission profile. Source 302 and detector array 502 rotate with gantry 14 (shown in FIGS. 1 and 2) around patient 22 such that an angle at which pencil-beam 304 intersects the patient 22 changes.

It is contemplated that the benefits of the various embodiments of the invention accrue to all multi-modality imaging systems, such as, for example, but not limited to, a CT/SPECT/PET imaging system.

The above-described multi-modality imaging systems provide a cost-effective and reliable means for examining a patient. More specifically, each imaging system includes configuration components that may be chosen to satisfy a particular imaging requirement, such as, but not limited to, component cost, image quality considerations, and component location limitations, such as gantry congestion. For example, a CT imaging system can complete a scan in a significantly shorter amount of time than a gamma camera can complete an emission scan. As such, during a multi-modality scan the CT imaging system may be inactive for a significant portion of the time it takes to complete the scan while waiting for the gamma camera to complete the emission portion of the scan. Accordingly, combining a slower scanning, high quality, inexpensive pencil-beam CT system with a gamma camera provides a cost-effective multi-modality system.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

While the invention has been described in terms of various specific embodiments, those skilled in the art will recognize that the invention can be practiced with modification within the spirit and scope of the claims.

What is claimed is:

1. A method for performing medical imaging, the method comprising:
   imaging a patient utilizing a computed tomography imaging modality, the patient between a pencil-beam x-ray source and an x-ray detector; and
   imaging the patient between the pencil-beam x-ray source and the x-ray detector using a nuclear medicine imaging modality.

2. A method in accordance with claim 1 wherein imaging the patient utilizing a nuclear medicine imaging modality and imaging the patient utilizing a computed tomography imaging modality are performed simultaneously.

3. A method in accordance with claim 1 wherein imaging the patient utilizing a nuclear medicine imaging modality and imaging the patient utilizing a computed tomography imaging modality are performed sequentially.

4. A method in accordance with claim 1 wherein imaging a patient utilizing a computed tomography imaging modality comprises translating at least one of the x-ray detector and the pencil-beam x-ray source laterally during a portion of a computed tomography scan.

5. A method in accordance with claim 1 wherein imaging a patient utilizing a computed tomography imaging modality comprises translating at least one of the x-ray detector and the pencil-beam x-ray source along an arcuate path during a portion of a computed tomography scan.

6. A method in accordance with claim 1 wherein imaging a patient utilizing a computed tomography imaging modality comprises translating the x-ray detector and the pencil-beam x-ray source during a portion of a computed tomography scan.

7. A method in accordance with claim 1 wherein imaging a patient utilizing a computed tomography imaging modality comprises maintaining a gantry, supporting the pencil-beam x-ray source and the x-ray detector, substantially stationary in at least one viewing position while translating at least one of the pencil-beam x-ray source and the x-ray detector from a first imaging position to a second imaging position.

8. A method in accordance with claim 1 wherein imaging a patient utilizing a computed tomography imaging modality comprises directing a pencil-beam of x-rays at a plurality of predetermined angles with respect to the pencil-beam x-ray source during a portion of a computed tomography scan.

9. A method in accordance with claim 1 wherein imaging a patient utilizing a computed tomography imaging modality comprises directing a pencil-beam of x-rays at a substantially fixed angle with respect to the pencil-beam x-ray source during a portion of a computed tomography scan.

10. A method in accordance with claim 1 further comprising rotating the pencil-beam x-ray source and x-ray detector around a longitudinal axis of a viewing area and within a predetermined angle.

11. A method in accordance with claim 10 wherein the nuclear medicine imaging modality includes an emission radiation detector, said method further comprising corotating the emission radiation detector around the longitudinal axis of the viewing area with the pencil-beam x-ray source and x-ray detector.

12. A method in accordance with claim 10 wherein the nuclear medicine imaging modality includes an emission radiation detector, said method further comprising rotating the emission radiation detector around the longitudinal axis of the viewing area separately from the pencil-beam x-ray source and x-ray detector.

13. A method in accordance with claim 1 wherein imaging the patient utilizing a nuclear medicine imaging modality comprises imaging the patient using at least one of single positron emission computed tomography (SPECT) and positron emission tomography (PET).

14. A method for multi-modality imaging comprising:
   scanning an area using a computed tomography imaging modality, the area between a pencil-beam x-ray source and an x-ray detector; and
   scanning the area using a nuclear medicine imaging modality.

15. A method for multi-modality imaging in accordance with claim 14 wherein scanning an area using a computed tomography imaging modality comprises maintaining a gantry, supporting the pencil-beam x-ray source and the x-ray detector, substantially stationary in at least one viewing position while translating at least one of the pencil-beam x-ray source and the x-ray detector from a first imaging position to a second imaging position.

16. A multi-modality computed tomography system, comprising:
   a gantry, rotatable about a viewing area;
   a x-ray source coupled to said gantry that provides a pencil-beam of x-rays, said x-ray source configured to direct at least a portion of the pencil-beam of x-rays into said viewing area;
   a detector that is responsive to said pencil-beam of x-rays and that is configured to receive at least a portion of said x-rays during a x-ray computed tomography portion of a scan; and
   at least one gamma camera configured to receive gamma photons emitted in said viewing area.

17. A multi-modality computed tomography system in accordance with claim 16 wherein said gantry is configured to maintain a stationary position, while at least one of said pencil-beam x-ray source and said x-ray detector are translated from a first imaging position to a second imaging position.

18. A multi-modality computed tomography system in accordance with claim 16 further comprising a second gantry positioned substantially parallel to said gantry and axially spaced from said gantry, said second gantry configured to rotate said at least one gamma camera about the viewing axis.

19. A multi-modality computed tomography system in accordance with claim 16 further comprising a second gamma camera positioned to receive coincident gamma photons emitted in said viewing area.

20. A multi-modality computed tomography system in accordance with claim 16 wherein said x-ray source provides a pencil-beam of x-rays at a plurality of angles with respect to said pencil-beam detector.

21. A multi-modality computed tomography system in accordance with claim 16 wherein said x-ray source provides a pencil-beam of x-rays at a substantially fixed angle with respect to said pencil-beam detector.

22. A multi-modality computed tomography system in accordance with claim 16 further comprising a translational mechanism coupled to said gantry, said translational mechanism configured move at least one of said x-ray source and said x-ray detector from a first position to a second position with respect to said gantry.

23. A multi-modality computed tomography system in accordance with claim 16 further comprising a translational mechanism associated with each of said x-ray source and said x-ray detector, each of said translational mechanisms coupled to said gantry, each of said translational mechanisms configured to move at least one of said x-ray source and said x-ray detector from a first position to a second position with respect to said gantry.

24. A multi-modality computed tomography system in accordance with claim 16 further comprising a translational mechanism associated with each of said x-ray source and said x-ray detector, each of said translational mechanisms coupled to said gantry, each of said translational mechanisms configured to move said x-ray source and said x-ray detector co-axially from a first position to a second position with respect to said gantry.

25. A multi-modality computed tomography system in accordance with claim 16 wherein said detector comprises a linear array of detector elements, said x-ray source configured to sweep a pencil-beam of x-rays in relation to said detector.

26. A multi-modality computed tomography system, comprising:
  a gantry, rotatable around a substantially rectangular viewing area;
  a x-ray source coupled to said gantry that provides a pencil-beam of x-rays, said x-ray source configured to direct at least a portion of the pencil-beam of x-rays into said viewing area, said x-ray source positioned adjacent a first side of the viewing area;
  a detector that is responsive to said pencil-beam of x-rays and that is configured to receive at least a portion of said x-rays during a x-ray computed tomography portion of a scan, said detector positioned on a second side of the viewing area opposite said first side; and
  a gamma camera configured to receive gamma photons emitted in said viewing area, said gamma camera positioned on at least one of a third side of the viewing area and a fourth side of the viewing area wherein the third and the fourth sides are each positioned between the first and second sides in an opposing arrangement.

27. A multi-modality computed tomography system in accordance with claim 26 wherein said gantry is configured to maintain a stationary position, while at least one of said pencil-beam x-ray source and said x-ray detector are translated from a first imaging position to a second imaging position.

28. A multi-modality computed tomography system in accordance with claim 26 wherein said x-ray source is configured to transmit a pencil-beam of x-rays at a substantially fixed angle with respect to the detector.

29. A multi-modality computed tomography system in accordance with claim 26 wherein said x-ray source is configured to sweep a pencil-beam of x-rays at a plurality of predetermined angles with respect to the detector.

30. A multi-modality computed tomography system in accordance with claim 26 wherein said x-ray detector is a linear array of detector elements configured to receive a beam of attenuated radiation from said x-ray source.

31. A multi-modality imaging system comprising:
  a pencil-beam x-ray computed tomography (CT) portion; and
  a nuclear medicine imaging portion.

32. A multi-modality imaging system in accordance with claim 31 further comprising a gantry supporting a pencil-beam x-ray source and a x-ray detector, said gantry configured to maintain a stationary position, while at least one of said pencil-beam x-ray source and said x-ray detector are translated from a first imaging position to a second imaging position.

33. A multi-modality imaging system in accordance with claim 31 further comprising:
  a first gantry supporting said pencil-beam x-ray CT portion; and
  a second gantry supporting said nuclear medicine imaging portion, said second gantry positioned substantially parallel to said first gantry, said second gantry axially spaced from said first gantry.

34. A multi-modality imaging system in accordance with claim 31 wherein said pencil-beam x-ray (CT) portion and said nuclear medicine imaging portion cooperate to perform a scan of a viewing area using a rotatable gantry.

35. A multi-modality imaging system in accordance with claim 31 wherein said pencil-beam x-ray (CT) portion and said nuclear medicine imaging portion are configured to perform a pencil-beam x-ray (CT) scan and a nuclear medicine imaging scan sequentially.

36. A multi-modality imaging system in accordance with claim 31 wherein said pencil-beam x-ray (CT) portion and said nuclear medicine imaging portion are configured to perform a pencil-beam x-ray (CT) scan and a nuclear medicine imaging scan simultaneously.

37. A multi-modality imaging system in accordance with claim 31 wherein said pencil-beam x-ray (CT) portion and said nuclear medicine imaging portion are configured to perform a scan alternating between at least a portion of a pencil-beam x-ray (CT) scan and at least a portion of a nuclear medicine imaging scan.

38. A multi-modality imaging system in accordance with claim 31 wherein said nuclear medicine imaging portion comprises at least one of a gamma camera, a positron emission tomography (PET) imaging system, and a single positron emission tomography (SPECT) system.

* * * * *